US008690774B2

(12) United States Patent
Ruether et al.

(10) Patent No.: US 8,690,774 B2
(45) Date of Patent: *Apr. 8, 2014

(54) ANALYZER FOR MEASURING BLOOD GAS PARAMETERS

(75) Inventors: Horst Ruether, Hart bei Graz (AT); Herfried Huemer, Feldbach (AT)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 803 days.

This patent is subject to a terminal disclaimer.

(21) Appl. No.: 12/273,749

(22) Filed: Nov. 19, 2008

(65) Prior Publication Data

US 2009/0163792 A1 Jun. 25, 2009

Related U.S. Application Data

(62) Division of application No. 10/449,420, filed on May 30, 2003, now Pat. No. 7,491,175.

(30) Foreign Application Priority Data

May 31, 2002 (AT) .................................. A 839/2002

(51) Int. Cl.
*A61B 5/00* (2006.01)
*A61B 19/00* (2006.01)

(52) U.S. Cl.
USPC ............................ 600/364; 600/549; 604/403

(58) Field of Classification Search
USPC ............................ 600/353, 364, 549; 422/81; 604/4.01–6.06, 6.13, 403–410, 415
See application file for complete search history.

(56) References Cited

U.S. PATENT DOCUMENTS

| 3,658,478 | A | | 4/1972 | Spergel et al. |
| 3,929,588 | A | * | 12/1975 | Parker et al. ............... 205/782.5 |
| 4,114,602 | A | | 9/1978 | Huch et al. |
| 4,290,431 | A | | 9/1981 | Herbert et al. |
| 4,420,564 | A | | 12/1983 | Tsuji et al. |
| 4,548,259 | A | | 10/1985 | Tezuka et al. |
| 4,717,548 | A | | 1/1988 | Lee |
| 4,929,426 | A | | 5/1990 | Bodai et al. |
| 5,232,667 | A | | 8/1993 | Hieb et al. |
| 6,669,661 | B1 | | 12/2003 | Yee |
| 6,890,757 | B2 | | 5/2005 | Kurkowski et al. |
| 7,491,175 | B2 | * | 2/2009 | Ruether et al. ................ 600/549 |
| 2002/0109621 | A1 | * | 8/2002 | Khair et al. ................... 341/174 |
| 2003/0209450 | A1 | * | 11/2003 | McVey et al. ................. 205/782 |
| 2005/0250995 | A1 | * | 11/2005 | Quy ............................. 600/300 |

FOREIGN PATENT DOCUMENTS

DE 2651356 A1 5/1978
WO WO 94/19684 A1 9/1994

* cited by examiner

*Primary Examiner* — Patricia Mallari
*Assistant Examiner* — Christian Jang
(74) *Attorney, Agent, or Firm* — Roche Diagnostics Operations, Inc.

(57) ABSTRACT

The invention relates to a method and device for measuring blood gas parameters, preferably pH, $pCO_2$, and $pO_2$, in a blood sample, where the blood sample of a patient is fed into at least one measuring cell of an analyzer. In order to obtain accurate values for the blood gas parameters even in cases where the temperature of the patient deviates from normal temperature, the temperature of the patient or blood sample is measured upon sample withdrawal, and the measured temperature is transmitted to the analyzer or is recorded by the analyzer, and the temperature of the measuring cell of the analyzer is adjusted to the measured temperature by cooling or heating.

7 Claims, 1 Drawing Sheet

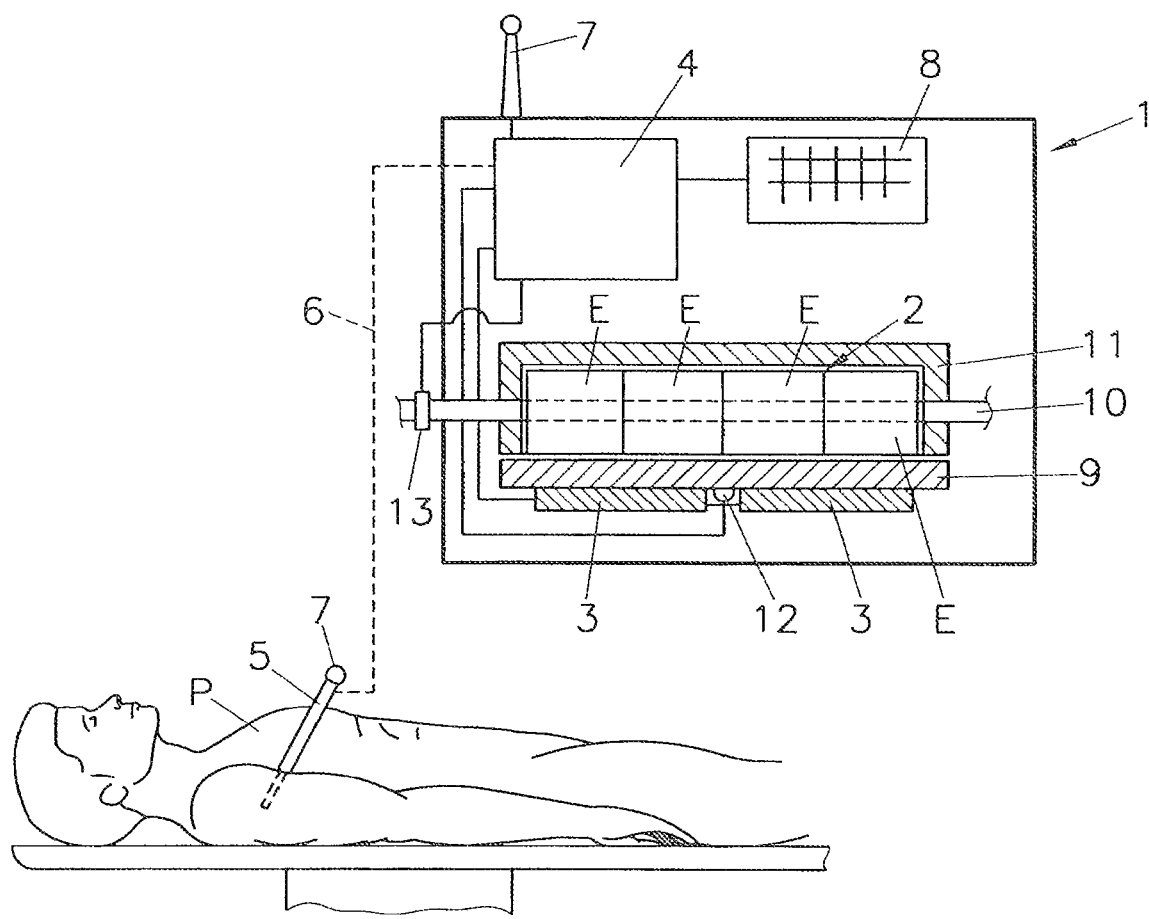

ANALYZER FOR MEASURING BLOOD GAS PARAMETERS

BACKGROUND OF THE INVENTION

The present invention relates generally to analytical test devices and, more particularly, to a method and device for measuring blood gas parameters, preferably pH, $pCO_2$, and $PO_2$, in a blood sample, where the blood sample of a patient is fed into at least one measuring cell of an analyzer.

In the blood gas multi-analyzers described in the literature and commercially available the measuring cells are thermostabilized at body temperature, i.e., at 37.0° C. Besides measuring the blood gas parameters pH, $pCO_2$ and $pO_2$, these analyzers are used to measure electrolytes, metabolic parameters and Hb-derivatives. For this reason the maximum operating temperature of such analyzers should always be somewhat lower than the temperature of the measuring cell and lies between 31° C. and 33° C. in commercially available devices.

In U.S. Pat. No. 4,548,259 A a measuring cell is described in the context of a chemical analyzer for photometric measurement of a liquid sample, which is thermostabilized by being provided on opposing walls with thermoelements, e.g., Peltier elements, the side walls of the measuring cell furthermore being provided with temperature sensors for measuring the cell temperature. After a sample has been fed into the measuring cell, the cell may be heated or cooled by means of the Peltier elements—depending on the output signal of the temperature sensors—until a predetermined working temperature in the range of 37° C.±0.2° C. is attained. The device described is suitable for the photometric measurement of blood samples, for instance, during which temperature must be kept constant.

From DE 26 51 356 A1 a measuring device for the photometry of liquid samples is known, in which a Peltier element is proposed as a heat-source or heat-sink for the thermostabilization of small measuring vessels (and thus small measurement samples). This permits rapid and highly accurate adjustment of the working temperature (preferably 30° C.) of the measuring device.

Finally, a blood gas analyzer is described in U.S. Pat. No. 4,717,548, which determines blood gas parameters, such as pH, $pCO_2$, $PO_2$ and temperature, in an extracorporeal blood flow situation, for instance during open-heart surgery, and which records the individual signals in real time. The signals are used for parameter monitoring and may activate alarm and switching functions when preset values are exceeded.

If conventional blood gas multi-analyzers are used for blood gas analysis with patients whose body temperature deviates from the normal temperature (37° C.), for instance in special surgery cases during which body temperature is artificially lowered, it is standard practice to correct the values for pH, $pCO_2$ and $pO_2$ obtained from the measuring device with the use of mathematical models, in order to find the medically relevant values at the actual body temperature of the patient. Such corrections are rather imprecise, however, and errors of up to 50% may occur.

SUMMARY OF THE INVENTION

It is against the above background that the present invention provides certain unobvious advantages and advancements over the prior art. In particular, the inventors have recognized a need for improvements in methods and devices for measuring blood gas parameters.

Although the present invention is not limited to specific advantages or functionality, it is noted that the present invention provides a method for measuring blood gas parameters, preferably pH, $pCO_2$ and $pO_2$, of a blood sample, and an analyzing device for application of the method, which permits the determining of accurate values for the blood gas parameters even in cases where the temperature of the patient deviates from normal temperature. The partial pressures ($pCO_2$, $pO_2$) and the pH-value are measured at the actual temperature of the patient, thus giving values which are of immediate physiological relevance, and rendering superfluous any error-prone subsequent mathematical correction of the measured values. The values obtained permit rapid medical action and provide a basis for emergency measures.

In accordance with one embodiment of the present invention, a method for measuring blood gas parameters in a blood sample from a patient is provided, comprising measuring the temperature of the patient or blood sample upon sample withdrawal, feeding the blood sample into at least one measuring cell of an analyzer for measuring blood gas parameters, transmitting the measured temperature to the analyzer, and adjusting the temperature of the at least one measuring cell of the analyzer to the measured temperature.

In accordance with another embodiment of the present invention, an analyzing device implementing the method of the invention is characterized by a regulating and control unit, which permits regulating the temperature of the measuring cell in the range from 22° C. to 40° C. depending on the temperature of the blood or the patient measured at the time of sampling.

The method according to the invention will permit a stable temperature regimen for the measuring cell even at operating or ambient temperatures which are higher than the temperature of the measuring cell.

The measuring cell can be cooled or heated to the measured temperature before the blood sample is entered into the analyzer and if sample entry is enabled only after this temperature is reached. During an operation the anesthetist or internist is assisted by this arrangement since the analyzer will automatically signal when sample entry may take place from the point of view of measurement accuracy.

The blood temperature or the temperature of the patient may be measured in the conventional way by means of a thermometer or measuring probe and entered manually into the analyzer via an entry device (keyboard or touchscreen). Measurement of the temperature, data entry into the analyzer, withdrawal of the blood sample and sample entry into the analyzer can all be effected within a time period of a few minutes, preferably.

The process can be automated in such a way that the blood or patient temperature is measured by a temperature probe adapted to be capable of being placed inside or on the patient, and the temperature data are transmitted automatically to the analyzer. In this case, the temperature of the measuring cell can be continually adjusted synchronously with the actual temperature measured. For this purpose the patient temperature may be measured on various parts of the body by means of thermometers, temperature sensors or infrared measuring cells. For accurately determining the basal temperature the placing of a sensor in the anal region is indicated.

The measurement signal can be amplified directly in the measuring probe, can be converted in an A/D-converter, and can be transmitted noise-free over a distance of a few meters to the analyzer interface as an IF or RF signal. Transmission via cable is also possible.

These and other features and advantages of the present invention will be more fully understood from the following detailed description of the invention taken together with the accompanying claims. It is noted that the scope of the claims is defined by the recitations therein and not by the specific discussion of features and advantages set forth in the present description.

BRIEF DESCRIPTION OF THE DRAWING

The following detailed description of the embodiments of the present invention can be best understood when read in conjunction with the following drawing, where like structure is indicated with like reference numerals and in which:

FIG. 1 is a schematic representation of an example of a device of the invention.

Skilled artisans appreciate that elements in the FIGURE are illustrated for simplicity and clarity and have not necessarily been drawn to scale. For example, the dimensions of some of the elements in the FIGURE may be exaggerated relative to other elements to help improve understanding of the embodiment(s) of the present invention.

DETAILED DESCRIPTION

The present invention will be further described below, with reference to the schematic representation in FIG. 1.

Reference numeral 1 denotes an analyzer for the measurement of blood gas parameters, preferably pH, $pCO_2$ and $pO_2$, in a blood sample, where the analyzer 1 has at least one thermostabilized measuring cell 2 with electrochemical measurement electrodes E, for instance flow sensors. The measuring cell 2 and measurement electrodes E, respectively, can be heated or cooled, for instance by means of Peltier elements 3, via a distributor element 9, which is a good heat conductor, depending on the output signal of a regulating and control device 4, which is connected to a temperature probe 5 placed in or on the patient P. The current temperature of the measuring cell 2, through which a sample capillary 10 runs and which is provided with thermal insulation 11, is recorded by a temperature sensor 12 whose measurement signal is fed to the regulating unit 4.

For data transmission to the regulating and control device 4 a cable 6 (dashed line) or a wireless link 7 is provided. Depending on the patient temperature measured by the temperature probe 5 the temperature of the measuring cell 2 can be regulated over a range of 22° C. to 40° C., the temperature of the measuring cell 2 preferably being continually and synchronously adjusted to the currently measured temperature of the patient P.

The patient temperature determined by measurement probe 5 may also be read off and entered into the analyzer 1 by means of an input device 8, for instance a keyboard.

Furthermore, the analyzer 1 may be provided with a locking device 13 on the sample input element, which is controlled by the regulating and control device 4 and enables sample input only when the temperature of the measuring cell 2 is equal to the blood or patient temperature measured.

It is noted that terms like "preferably", "commonly", and "typically" are not utilized herein to limit the scope of the claimed invention or to imply that certain features are critical, essential, or even important to the structure or function of the claimed invention. Rather, these terms are merely intended to highlight alternative or additional features that may or may not be utilized in a particular embodiment of the present invention.

For the purposes of describing and defining the present invention it is noted that the term "substantially" is utilized herein to represent the inherent degree of uncertainty that may be attributed to any quantitative comparison, value, measurement, or other representation. The term "substantially" is also utilized herein to represent the degree by which a quantitative representative may vary from a stated reference without resulting in a change in the basic function of the subject matter at issue.

Having described the invention in detail and by reference to specific embodiments thereof, it will be apparent that modifications and variations are possible without departing from the scope of the invention defined in the appended claims. More specifically, although some aspects of the present invention are identified herein as preferred or particularly advantageous, it is contemplated that the present invention is not necessarily limited to these preferred aspects of the invention.

What is claimed is:

1. An analyzer comprising:
   at least one measuring cell;
   a temperature sensor for measuring the temperature of the measuring cell;
   elements for heating and cooling the measuring cell;
   a regulating unit for adjusting the temperature of the measuring cell to the temperature of a patient or blood sample upon sample withdrawal;
   a temperature probe for measuring the temperature of the patient or blood sample, wherein the regulating unit is connected to the temperature probe via a cable or wireless link for data transmission from the probe to the regulating unit; and
   a locking device on a sample input element, wherein the regulating unit enables sample input only when the measuring cell temperature is equal to the blood sample temperature or patient temperature.

2. The analyzer of claim 1, wherein the wireless link comprises an infrared or a radio frequency signal.

3. The analyzer of claim 1, wherein the regulating unit is configured to adjust the temperature of the measuring cell between about 22 and about 40° C.

4. The analyzer of claim 1 further comprising an electrochemical measurement electrode configured for measuring at least one blood gas parameter in the blood sample, wherein the blood gas parameter is selected from pH, $pCO_2$, $pO_2$, and combinations thereof.

5. An analyzer comprising:
   at least one measuring cell;
   a temperature sensor for measuring the temperature of the measuring cell;
   elements for heating and cooling the measuring cell;
   a regulating unit for adjusting the temperature of the measuring cell to the temperature of a patient or blood sample upon sample withdrawal; and
   a temperature probe for measuring the temperature of the patient or blood sample, wherein
      the regulating unit is connected to the temperature probe via a cable or wireless link for data transmission from the probe to the regulating unit, and
      the analyzer enables the blood sample to enter the measuring cell only if the temperature of the measuring cell is substantially equal to the measured temperature of the patient or blood sample upon sample withdrawal.

6. The analyzer of claim 5, wherein the temperature of the measuring cell is adjusted to the measured temperature of the patient or blood sample upon sample withdrawal, before the analyzer enables the blood sample to enter the measuring cell.

7. An analyzer comprising:
   at least one measuring cell;
   a temperature sensor for measuring the temperature of the measuring cell;

elements for heating and cooling the measuring cell;
a regulating unit for adjusting the temperature of the measuring cell to the temperature of a patient or blood sample upon sample withdrawal; and
a temperature probe for continuously measuring the temperature of the patient or blood sample, wherein
 the regulating unit is connected to the temperature probe via a cable or wireless link for data transmission from the probe to the regulating unit, and
 the regulating unit is configured to continually adjust the temperature of the measuring cell synchronously with the measured temperature of the patient.

\* \* \* \* \*